United States Patent [19]

Yokobe et al.

[11] 4,358,407

[45] Nov. 9, 1982

[54] BENZOTHIAZINE DERIVATIVES

[75] Inventors: Tetsuo Yokobe, Nakatsu; Mitsuru Masago, Kashihara; Yasuaki Chihara, Yoshitomimachi; Yutaka Maruyama, Nakatsu, all of Japan

[73] Assignee: Yoshitomi Pharmaceutical Industries Ltd., Japan

[21] Appl. No.: 295,578

[22] PCT Filed: Dec. 17, 1980

[86] PCT No.: PCT/JP80/00309

§ 371 Date: Aug. 24, 1981

§ 102(e) Date: Aug. 24, 1981

[87] PCT Pub. No.: WO81/01848

PCT Pub. Date: Jul. 9, 1981

[51] Int. Cl.³ ............... C07D 513/22; C07D 515/22
[52] U.S. Cl. .................................. 260/243.3; 544/14
[58] Field of Search ............... 544/14; 424/246; 260/243.3

[56] References Cited

U.S. PATENT DOCUMENTS 3,555,018 1/1971 Davis ............................ 544/14
4,219,550 8/1980 Rajagopalan .................. 544/14

Primary Examiner—John M. Ford
Attorney, Agent, or Firm—Larson and Taylor

[57] ABSTRACT

Benzothiazine derivatives represented by the formula

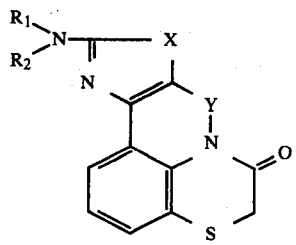

wherein $R_1$ is hydrogen, alkyl, alkoxycarbonyl, alkoxalyl, phenyl which may optionally have a substituent or substituents, cycloalkyl or aralkyl, $R_2$ is hydrogen or alkyl, X is sulphur or oxygen, and Y is methylene or ethylene, and acid addition salts thereof. These compounds are useful as analgesic agents, anti-inflammatory agents, anti-allergic agents, anti-arthritic agents, circulation-improving agents or like pharmaceutics.

9 Claims, No Drawings

BENZOTHIAZINE DERIVATIVES

TECHNICAL FIELD AND DISCLOSURE OF THE INVENTION

This invention relates to novel benzothiazine derivatives represented by the formula

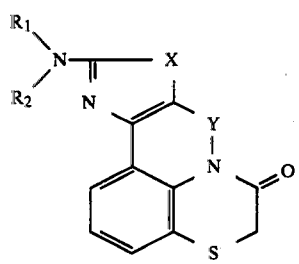

(I)

wherein $R_1$ is hydrogen, alkyl, alkoxycarbonyl, alkoxalyl, phenyl which may optionally have a substituent or substituents, cycloalkyl or aralkyl, $R_2$ is hydrogen or alkyl, X is sulphur or oxygen, and Y is methylene or ethylene, and acid addition salts thereof, and also concerns with processes for preparing them.

Hereinafter the symbols in the formula (I) are more specifically described. The alkyl groups in the formula (I) refer to straight-chain or branched groups having 1 to 10 carbon atoms such as methyl, ethyl, propyl, isopropyl, butyl, isobutyl, sec-butyl, tert-butyl, pentyl, octyl, nonyl, decyl, etc. Examples of the cycloalkyl groups in the formula (I) are cyclopropyl, cyclopentyl, cyclohexyl, etc. Examples of the alkoxycarbonyl groups therein are methoxycarbonyl, ethoxycarbonyl, propoxycarbonyl, butoxycarbonyl, etc. The alkoxalyl groups therein include methoxalyl, ethoxalyl, propoxalyl and butoxalyl. The phenyl groups which may have a substituent or substituents are those which may have 1 to 3 substituents such as halogen (e.g. chlorine or bromine), lower alkyl (e.g. methyl, ethyl, propyl or butyl) or lower alkoxy (e.g. methoxy, ethoxy, propoxy, butoxy or methylenedioxy) at optional position(s) in optional combinations. Examples of the aralkyl groups are α-methylbenzyl, phenetyl, etc.

The compounds represented by the formula (I) are prepared for example by processes as described below.

Process 1

This process comprises the step of reacting a compound having the formula

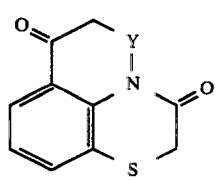

(II)

with an iodine and a compound having the formula

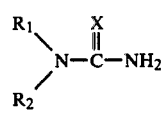

(III)

The symbols in the formulae (II) and (III) are as defined above.

This reaction is conducted in an inactive solvent (such as chloroform, dioxane and dimethylformamide) or without a solvent at room temperature or, when required, by heating.

Process 2

This process comprises the steps of reacting the compound of the formula (II) with a halogen to prepare a compound represented by the formula

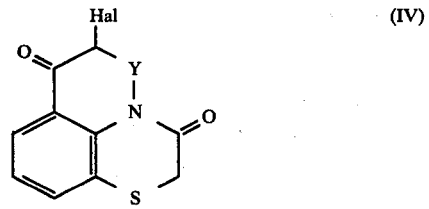

(IV)

wherein Hal is bromine, chlorine or like halogens and Y is as defined above and reacting the compound of the formula (IV) with the compound of the formula (III).

This reaction is carried out in an inactive solvent (such as chloroform, ether, dioxane, ethanol or a mixture thereof) at room temperature or, if required, by heating the solvent up to its boiling point.

Process 3

This process is used to prepare compounds of the formula (I) wherein $R_1$ is alkyl, cycloalkyl, alkoxycarbonyl, alkoxalyl, aralkyl and $R_2$ is hydrogen, namely compounds of the formula

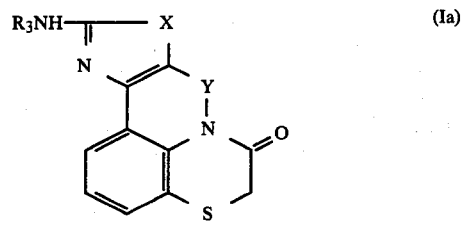

(Ia)

wherein $R_3$ is alkyl, cycloalkyl, alkoxycarbonyl, alkoxalyl, aralkyl, and X and Y are as defined above. The process comprises the step of reacting a compound represented by the formula

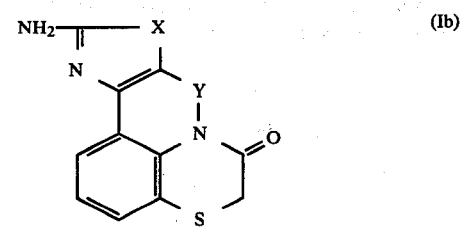

(Ib)

wherein X and Y are as defined above with a compound of the formula $R_3-Z$ (V)

wherein Z is chlorine, bromine, methylsulfonyloxy, p-tolylsulfonyloxy or like reactive residues, and $R_3$ is as defined above.

This reaction is usually effected in an inactive solvent (such as methanol, ethanol, dioxane or dimethylformamide) and, if required, in the presence of a deoxidizer (such as pyridine, triethylamine or like organic bases, or sodium carbonate, potassium carbonate, sodium bicarbonate, sodium hydroxide, potassium hydroxide or like inorganic bases) at room temperature or by heating the solvent up to its boiling point.

Process 4

This process is used to prepare compounds of the formula (I) wherein $R_2$ is alkyl, namely compounds of the formula

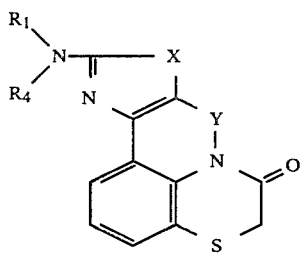 (Ic)

wherein $R_4$ is alkyl, and $R_1$, X and Y are as defined above. The process comprises the step of reacting a compound of the formula

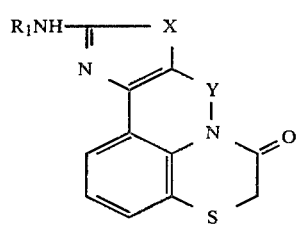 (Id)

wherein the symbols are as defined above with a compound of the formula $R_4—Z$ (VI)

wherein the symbols are as defined above.

The reaction is carried out under the same conditions as in Process 3.

Process 5

This process is used to prepare compounds of the formula (I) wherein $(R_1)(R_2)N—$ is $(R_5)(R_6)CHNH—$, namely compounds of the formula

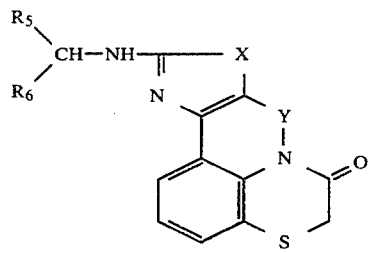 (Ie)

wherein $R_5$ is hydrogen, alkyl, phenyl or aralkyl, $R_6$ is alkyl, phenyl or aralkyl, $R_5$ and $R_6$ form alkylene when taken together, and X and Y are as defined above to reduce a compound of the formula

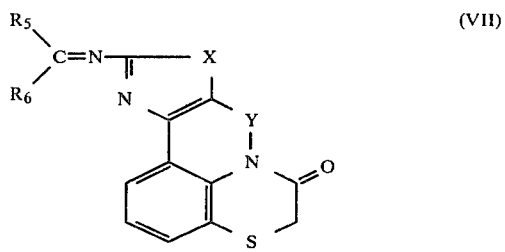 (VII)

wherein the symbols are as defined above.

This reduction can be conducted by a process which is usually used for reducing a Schiff base. For instance, the compound is reduced in a solvent such as methanol, ethanol, isopropanol, water, dioxane or tetrahydrofuran by using a sodium boron hydride or like alkali boron hydride. Alternatively this can be done by a catalytic reduction, e.g. in a solvent such as methanol, ethanol, dioxane or tetrahydrofuran by using palladium-carbon, Raney nickel, platinum oxide or like metal catalysts at atmospheric or increased pressure.

The compounds of the formula (VII) serving as the material are prepared by reacting a compound of the formula

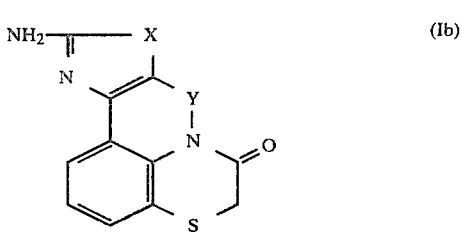 (Ib)

wherein X and Y are as defined above with a compound of the formula

 (VIII)

wherein $R_5$ and $R_6$ are as defined above in an inactive solvent (such as benzene, toluene, chloroform or tetrahydrofuran) or without a solvent at room temperature or if necessary by heating, or if required in the presence of paratoluenesulfonic acid, hydrochloric acid, sulfuric acid or like catalysts, and removing the water azeotropically produced.

The compounds are reduced also by mixing the compound (Ib) with the compound (VIII) in a solvent such as methanol, ethanol or tetrahydrofuran and, if required, stirring the reaction mixture with heating, without separating the Schiff base from the reaction product.

The novel compounds of the formula (II) serving as the material are prepared in the conventional manner for example ① by converting a compound of the formula

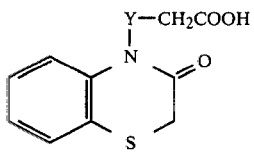

wherein Y is as defined as above into an acid halide by the action of a halogenating agent (such as thionyl chloride, thionyl bromide, phosphorus trichloride, phosphorus tribromide or phosphorus oxychloride) to subject the acid halide to the Friedel-Crafts reaction or 2 by subjecting the compound of the formula (IX) directly to a condensation reaction by using a polyphosphoric acid or the ester thereof.

The compounds of the formula (I) can be made into acid addition salts thereof by being treated with an acid. The acids useful for the formation of acid addition salts thereof are not particularly limited insofar as in general the acids are pharmacologically harmless as a medicament. Examples of useful acids are hydrochloric acid, hydrobromic acid, sulfuric acid, phosphoric acid or like inorganic acids, acetic acid, lactic acid, maleic acid, fumaric acid, oxalic acid, tartaric acid, citric acid, methanesulfonic acid, ethanesulfonic acid or like organic acids, etc. The type of acid to be used is determined according to the specific purpose of improving the stability or absorbing properties of the base or rendering the compound soluble or sparingly soluble in water.

The benzothiazine derivatives of the formula (I) and the acid addition salts thereof have analgesic activity, anti-inflammatory activity, anti-allergic activity, immunity controlling activity, anti-ischemia activity and hypoxia activity. For example, these compounds are useful as analgesic agents, anti-inflammatory agents, anti-allergic agents, anti-arthritic agents and circulation-improving agents.

When used as the active components of such pharmaceutical compositions, the compounds of the present invention are mixed with pharmaceutically acceptable excipients, and the pharmaceutical preparations thus prepared are orally or parenterally administered in the form of powders, granules, tablets, capsules and injection solutions. The dose of the pharmaceutical preparations depends on the type of the disease and symptom of the patient, and the kind of the compound of the present invention contained therein. Generally the preparation of the present invention, when orally administered, is given to an adult patient at a dose of about 1 to about 1,000 mg, preferably about 25 to about 500 mg, per day.

The present invention is hereinafter described in more detail with reference to examples but is not limited thereto.

EXAMPLE 1

A 10.0 g quantity of 2,3,5,6,7,8-hexahydro-[1,4]thiazino[2,3,4-jk][1]benzoazepine-3,8-dione was dissolved in 100 ml of chloroform and 50 ml of ether. To the solution was dropwise added 7.2 g of bromine with stirring at room temperature. After the addition, the mixture was stirred at room temperature for 2 hours. After the completion of the reaction, the reaction liquid was poured into 100 ml of water, and an aqueous solution of saturated sodium bicarbonate was added to the mixture to render the resulting mixture alkaline. Then the organic layer was separated from the mixture by a separatory funnel and dried over magnesium sulfate. Subsequently the chloroform and ether was distilled off at reduced pressure to obtain a crystal. The chrystal thus prepared was recrystallized from a chloroform-hexane mixture, affording 11 g of crystal of 7-bromo-2,3,5,6,7,8-hexahydro-[1,4]thiazino[2,3,4-jk][1]benzoazepine-3,8-dione, m.p. 144°–146° C.

EXAMPLE 2

To 30 ml of ethanol was added 2.98 g of 7-bromo-2,3,5,6,7,8-hexahydro-[1,4]-thiazino[2,3,4-jk][1]benzoazepine-3,8-dione. To the mixture was added 1.0 g of thiourea dissolved in 5 ml of water, with stirring at room temperature. The resulting mixture was gradually heated and stirred at 80° C. for 2 hours. After cooling, the crystal precipitated in the reaction liquid was filtered off, giving 3.1 g of crystal of 2-amino-4,5,7,8-tetrahydro-[1,4]thiazino[2,3,4-jk]thiazolo[5,4-d][1]benzoazepine-7-one hydrobromide, m.p. 308°–310° C. (decomposition).

EXAMPLE 3

A 10.0 g quantity of 7-bromo-2,3,5,6,7,8-hexahydro-[1,4]-thiazino[2,3,4-jk][1]benzoazepine-3,8-dione and 50.0 g of urea were gradually heated under stirring to undergo a melting reaction at 140° C. for 1 hour. After cooling, the reaction mixture was poured into 300 ml of water to filter off the water-insoluble crystal. The crystal thus obtained was recrystallized from a chloroform-methanol mixture, giving 2.5 g of crystal of 2-amino-4,5,7,8-tetrahydro-[1,4]thiazino[2,3,4-jk]oxazolo[5,4-d][1]benzoazepine-7-one, m.p. 275°–278° C.

EXAMPLE 4

A 5.0 g quantity of 2-amino-4,5,7,8-tetrahydro[1,4]-thiazino[2,3,4-jk]oxazolo[5,4-d][1]benzoazepine-7-one was dissolved in 80 ml of chloroform and 9.0 g of triethylamine. While the mixture was stirred with ice cooling, 5.0 g of ethoxalyl chloride was dropwise added thereto. After the addition, the mixture was heated up to 40° C. and stirred for 40 minutes. After cooling, the reaction liquid was poured into 100 ml g of water to separate off the organic layer. The organic layer was dried over magnesium sulfate and the chloroform was distilled off at reduced pressure. The oil thus obtained was purified by a silica gel column chromatography, giving 2.3 g of 2-ethoxalylamino-4,5,7,8-terahydro[1,4]thiazino[2,3,4-jk]oxazolo[5,4-d][1]benzoazepine-7-one in the form of crystal, m.p. 164°–165° C.

EXAMPLE 5

A 2.89 g quantity of 2-amino-4,5,7,8-tetrahydro[1,4]-thiazino[2,3,4-jk]thiazolo[5,4-d][1]benzoazepine-7-one was dissolved in 30 ml of dimethylform amide. To the solution was added 10 g of triethylamine. Then 1.37 g of n-butyl bromide was dropwise added to the mixture with stirring at room temperature. After the addition, the resulting mixture was gradually heated and stirred at 70° to 80° C. for 3 hours. After cooling, the reaction liquid was poured into 100 ml of water. Then the mixture was extracted with two 30 ml portions of chloroform. The organic layer was dried over magnesium sulfate and the chloroform was distilled off at reduced pressure. The oil thus obtained was purified by a silica gel column chromatography, affording 0.7 g of oil of 2-n-butyl amino-4,5,7,8-tetrahydro[1,4]thiazono[2,3,4-jk]thiazolo[5,4-d][1]benzoazepine-7-one. The hydrochloride was in the form of crystal melting at 238°–241° C.

EXAMPLE 6

A 3.12 g quantity of 2,3,5,6,7,8-hexahydro[1,4]-thiazino[2,3,4-jk][1]benzoazepine-3,8-dione, 10 ml of dioxane, 1.5 g of thiourea and 2.53 g of iodine were heated and stirred at 100° C. for 12 hours. After cooling, the reaction liquid was poured into 20 ml of 5% aqueous solution of sodium hydroxide. Then the mixture was extracted with two 20 ml portions of chloroform. The organic layer was dried over magnesium sulfate and the chloroform was distilled off at reduced pressure. The residue was purified by a silica gel column chromatography, affording 2-amino-4,5,7,8-tetrahydro-[1,4]thiazino[2,3,4-jk]thiazolo[5,4-d][1]benzoazepine-7-one in the form of crystal, m.p. 264°–267° C.

EXAMPLE 7

A 5.0 g quantity of 2-amino-4,5,7,8-tetrahydro[1,4]-thiazino[2,3,4-jk]thiazolo[5,4-d][1]benzoazepine-7-one and 5.0 g of benzaldehyde were dissolved in 50 ml of chloroform and 50 ml of methanol. Then the solution was refluxed with heating for 6 hours. After the completion of the reaction, the solvent was distilled off from the reaction liquid whereby the residue remained as a crystal. The crystal was filtered off and recrystallized from a chloroform-hexane mixture, giving 6.0 g of crystal of 2-benzylideneamino-4,5,7,8-tetrahydro-[1,4]thiazino[2,3,4-jk]thiazolo[5,4-d][1]benzoazepine-7-one.

A 6.0 quantity of 2-benzylideneamino-4,5,7,8-tetrahydro-[1,4]thiazino[2,3,4-jk]thiazolo[5,4-d][1]benzoazepine-7-one was suspended in 70 ml of methanol with stirring. To the suspension was added 4.0 g of sodium boron hydride by portions. After the addition, the reaction liquid was refluxed with heating under stirring for 2 hours. After the completion of the reaction, the solvent was distilled away and the residue was poured into 100 ml of water. Then the mixture was extracted with 100 ml of chloroform. The chloroform layer was separated off and dried over magnesium sulfate. At reduced pressure, the chloroform was distilled off, and the crystal precipitated was filtered off and recrystallized from a chloroform-hexane mixture, giving 4.0 g of crystal of 2-benzylamino-4,5,7,8-tetrahydro[1,4]thiazino[2,3,4-jk]thiazolo[5,4-d][1]benzoazepine-7-one, m.p. 185°–188° C.

EXAMPLE 8

A 5.0 g quantity of 2-amino-4,5,7,8-tetrahydro[1,4]-thiazino[2,3,4-jk]thiazolo[5,4-d][1]benzoazepine-7-one and 5.0 g of propionaldehyde were dissolved in a solvent mixture of 50 ml of chloroform and 50 ml of ethanol. Then the solution was refluxed with heating for 1 hour. After the completion of the reaction, the solvent was distilled off from the reaction liquid, giving 2-propylidene-amino-4,5,7,8-tetrahydro[1,4]-thiazino[2,3,4-jk]thiazolo[5,4-d][1]benzoazepine-7-one in the form of oil. The oil was dissolved in 50 ml of methanol, and to the solution was added 2.0 g of sodium boron hydride by portions over a period of about 30 minutes while being stirred at room temperature. Then for 2 hours, the mixture was refluxed with heating under stirring. After cooling, the methanol was distilled off from the reaction liquid at reduced pressure, and the residue was poured into 100 ml of water. The mixture was extracted with 100 ml of chloroform. The chloroform layer was dried over magnesium sulfate and the chloroform was distilled off at reduced pressure. The residue was purified by a silica gel column chromatography, giving 3.0 g of oil of 2-propylamino-4,5,7,8-tetrahydro-[1,4]thiazino[2,3,4-jk]thiazolo[5,4-d][1]benzoazepine-7-one. The hydrochloride was in the form of crystal melting at 237° to 241° C.

EXAMPLE 9

A 5.0 g quantity of 2-amino-4,5,7,8-tetrahydro[1,4]-thiazino[2,3,4-jk]thiazolo[5,4-d][1]benzoazepine-7-one and 5.0 g of octylaldehyde were dissolved in 50 ml of chloroform and 50 ml of methanol. To the solution was added 2.0 g of sodium boron hydride by portions over a period of about 1 hour. Then the mixture was refluxed with heating under stirring for 2 hours. After cooling, the solvent was distilled off from the reaction liquid at reduced pressure and the residue was poured into 100 ml of water. Then the mixture was extracted with 100 ml of chloroform. The chloroform layer was dried over magnesium sulfate and the chloroform was distilled off at reduced pressure. Subsequently the residue was purified by a silica gel column chromatography, giving 2.7 g of oil of 2-octylamino-4,5,7,8-tetrahydro-1,4-thiazino[2,3,4-jk]thiazolo[5,4-d][1]benzoazepine-7-one. The hydrochloride was in the form of crystal melting at 167°–169° C.

The compounds described below can be prepared in the same manner as in the examples.

2-Anilino-4,5,7,8-tetrahydro-[1,4]thiazino[2,3,4-jk]thiazolo[5,4-d][1]benzoazepine-7-one, hydrobromide melting at 290°–297° C. (decomposition)

2-Ethoxalylamino-4,5,7,8-tetrahydro[1,4]-thiazino[2,3,4-jk]thiazolo[5,4-d][1]benzoazepine-7-one, m.p. 250°–252° C.

2-Amino-6,7-dihydro-4H-[1,4]thiazino[2,3,4-jk]thiazolo[5,4-c]quinoline-6-one, m.p. 235°–237° C.

2-Ethoxycarboxyamide-4,5,7,8-tetrahydro-[1,4]thiazino[2,3,4-jk]thiazolo[5,4-d][1]benzoazepine-7-one, ½-hydrate melting at 155°–157° C.

2-Methylamino-4,5,7,8-tetrahydro-[1,4]thiazino[2,3,4-jk]thiazolo[5,4-d][1]benzoazepine-7-one, hydrobromide melting at 290°–294° C. (decomposition)

2-Isopropylamino-4,5,7,8-tetrahydro-[1,4]thiazino[2,3,4-jk]thiazolo[5,4-d][1]benzoazepine-7-one, m.p. 168°–170° C.

2-Pentylamino-4,5,7,8-tetrahydro-[1,4]thiazino[2,3,4-jk]thiazolo[5,4-d][1]benzoazepine-7-one, hydrochloride melting at 208°–211° C.

2-Cyclohexylamino-4,5,7,8-tetrahydro-[1,4]thiazino[2,3,4-jk]thiazolo[5,4-d][1]benzoazepine-7-one, hydrobromide melting at 260°–262° C.

2-Dimethylamino-4,5,7,8-tetrahydro-[1,4]thiazino[2,3,4-jk]thiazolo[5,4-d][1]benzoazepine-7-one, m.p. 191°–193° C.

2-[(4-Methoxyphenyl)amino)]-4,5,7,8-tetrahydro[1,4]thiazino[2,3,4-jk]thiazolo[5,4-d][1]benzoazepine-7-one, hydrobromide melting at 255°–257° C. (decomposition)

Although the present invention is fully disclosed in the specification and in the examples contained therein, different variations and modifications of the invention may be made without departing from the spirit and scope thereof.

We claim:

1. A compound of the formula

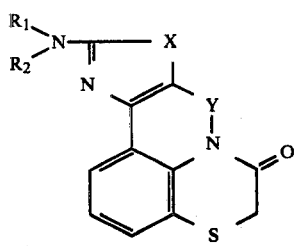

wherein R₁ is hydrogen, alkyl, alkoxycarbonyl, alkoxalyl, cycloalkyl, aralkyl and phenyl which may have 1 to 3 substituents at optional position(s) in optional combinations, each substituent being selected from the group consisting of halogen, lower alkyl and lower alkoxy, R₂ is hydrogen or alkyl, X is sulphur or oxygen, and Y is methylene or ethylene, and acid addition salts thereof.

2. A compound as defined in claim 1 which is 2-amino-4,5,7,8-tetrahydro-[1,4]thiazino[2,3,4-jk]thiazolo[5,4-d][1]benzoazepine-7-one.

3. A compound as defined in claim 1 which is 2-amino-4,5,7,8-tetrahydro[1,4]thiazino[2,3,4-jk]oxazolo[5,4-d][1]benzoazepine-7-one.

4. A compound as defined in claim 1 which is 2-n-butylamino-4,5,7,8-tetrahydro-[1,4]thiazino[2,3,4-jk]thiazolo[5,4-d][1]benzoazepine-7-one.

5. A compound as defined in claim 1 which is 2-propylamino-4,5,7,8-tetrahydro-[1,4]-thiazino[2,3,4-jk]thiazolo[5,4-d][1]benzoazepine-7-one.

6. A compound as defined in claim 1 which is 2-ethoxalylamino-4,5,7,8-tetrahydro-[1,4]thiazino[2,3,4-jk]thiazolo[5,4-d][1]benzoazepine-7-one.

7. A compound as defined in claim 1 which is 2-amino-6,7-dihydro-4H-[1,4]thiazino[2,3,4-ij]thiazolo[5,4-c]quinoline-6-one.

8. A compound as defined in claim 1 which is 2-isopropylamino-4,5,7,8-tetrahydro-[1,4]thiazino[2,3,4-jk]thiazolo[5,4-d][1]benzoazepine-7-one.

9. A compound as defined in claim 1 which is 2-dimethylamino-4,5,7,8-tetrahydro-[1,4]thiazino[2,3,4-jk]thiazolo[5,4-d][1]benzoazepine-7-one.

* * * * *